(12) United States Patent
Leem et al.

(10) Patent No.: US 11,758,810 B2
(45) Date of Patent: Sep. 12, 2023

(54) FLUORESCENT PROTEIN ACTIVATED SILK USED IN PHOTOELECTRIC CONVERSION

(71) Applicant: Purdue Research Foundation, West Lafayette, IN (US)

(72) Inventors: Jung Woo Leem, West Lafayette, IN (US); Seung Ho Choi, West Lafayette, IN (US); Young L. Kim, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 716 days.

(21) Appl. No.: 15/874,869

(22) Filed: Jan. 18, 2018

(65) Prior Publication Data

US 2018/0226594 A1 Aug. 9, 2018

Related U.S. Application Data

(60) Provisional application No. 62/593,976, filed on Dec. 3, 2017, provisional application No. 62/448,332, filed on Jan. 19, 2017.

(51) Int. Cl.
*H10K 85/00* (2023.01)
*C09K 11/06* (2006.01)
(Continued)

(52) U.S. Cl.
CPC ........... *H10K 85/761* (2023.02); *A23B 7/015* (2013.01); *A23B 7/154* (2013.01); *A61L 2/0052* (2013.01);
(Continued)

(58) Field of Classification Search
CPC ........... H02G 9/20–2095; H10K 85/00; H10K 85/761; H10K 30/30; H10K 30/82; H10K 2102/00; H10K 2102/10; H10K 2102/101; H10K 2102/102; H10K 2102/103; H01G 9/2018; H01G 9/2059; C07K 14/43586; C07K 14/43563; C07K 14/43504; C07K 19/00; C07K 2319/00; B01D 46/66; B01D 29/62; A23B 7/015; A23B 7/154; A61L 2/0052; A61L 2/0076; A61L 2/084; A61L 2/088; A61N 5/062; A61N 5/0624; A61N 2005/0663; A23V 2002/00
(Continued)

(56) References Cited

U.S. PATENT DOCUMENTS

2006/0180197 A1* 8/2006 Gui .................. H01G 9/2031
136/255

OTHER PUBLICATIONS

Long et al. "New insight into the mechanism underlying fibroin secretion in silkworm, *Bombyx mori*." FEBS Journal 282 (2015) 89-101. (Year: 2015).*

(Continued)

*Primary Examiner* — Mayla Gonzalez Ramos
(74) *Attorney, Agent, or Firm* — Piroozi-IP, LLC

(57) ABSTRACT

A photoelectric device is disclosed. The photoelectric device includes a first electrode, a second electrode, and an electrolyte disposed between the first electrode and the second electrode. The second electrode includes a transparent layer for allowing light to penetrate into the second electrode, an electron transport layer coupled to the transparent layer, and a genetically hybridized fluorescent silk layer as a photosensitizer coupled to the electron transport layer.

20 Claims, 13 Drawing Sheets

Specification includes a Sequence Listing.

(51) Int. Cl.
| | |
|---|---|
| H01G 9/20 | (2006.01) |
| C07K 14/435 | (2006.01) |
| H10K 30/30 | (2023.01) |
| H10K 30/82 | (2023.01) |
| A23B 7/015 | (2006.01) |
| A23B 7/154 | (2006.01) |
| A61L 2/00 | (2006.01) |
| A61L 2/08 | (2006.01) |
| A61N 5/06 | (2006.01) |
| C07K 19/00 | (2006.01) |
| H10K 102/00 | (2023.01) |
| H10K 102/10 | (2023.01) |
| B01D 46/66 | (2022.01) |
| B01D 29/62 | (2006.01) |

(52) U.S. Cl.
CPC ............ *A61L 2/0076* (2013.01); *A61L 2/084* (2013.01); *A61L 2/088* (2013.01); *A61N 5/062* (2013.01); *A61N 5/0624* (2013.01); *B01D 29/62* (2013.01); *B01D 46/66* (2022.01); *C07K 14/43504* (2013.01); *C07K 14/43586* (2013.01); *C07K 19/00* (2013.01); *C09K 11/06* (2013.01); *H01G 9/2018* (2013.01); *H10K 30/30* (2023.02); *H10K 30/82* (2023.02); *A23V 2002/00* (2013.01); *A61N 2005/0663* (2013.01); *C07K 2319/00* (2013.01); *C09K 2211/14* (2013.01); *H01G 9/2059* (2013.01); *H10K 2102/00* (2023.02); *H10K 2102/102* (2023.02); *H10K 2102/103* (2023.02); *Y02E 10/549* (2013.01)

(58) Field of Classification Search
USPC ........................................................ 136/263
See application file for complete search history.

(56) References Cited

OTHER PUBLICATIONS

Acikgoz et al., "Photoinduced electron transfer mechanism between green fluorescent protein molecules and metal oxide nanoparticles", Ceramics international, 2014..*
Mahyad et al., Bio-nano hybrid materials based on bacteriorhodopsin: Potential applications and future strategies, Advances in Colloid and Interface Science, 2015, 194-202, Elsevier B.V.
Choi et al., Charge trap in self-assembled monolayer of cytochrome b562-green fluorescent protein chimera, Current Applied Physics, 2005, 760-765, Elsevier B.V.
Tulachan et al., Electricity from the Silk Cocoon Membrane, Scientific Reports, 2014.
Salih, Fluorescence control in natural green fluorescent protein (GFP)-based photonic structures of reef corals, 2012, 199-234, Woodhead Publishing Limited.
Chuang et al., Fluorescent protein red Kaede chromophore; one-step, high-yield synthesis and potential application for solar cells, ChemComm., 2009, 6982-6984, The Royal Society of Chemistry.
Choi et al., Molecular rectifier consisting of cytochrome c/GFP heterolayer by using metal coated optical fiber tip, Current Applied Physics, 2005, 839-843, Elsevier B.V.
Choi et al., Molecular-scale biophotodiode consisting of a green fluorescent protein/cytochrome c self-assembled heterolayer. Applied Physics Letters, 2004, 2187-2189, vol. 84, No. 12, American Institute of Physics.
Deepankumar et al., Next Generation Designed Protein as a Photosensitizer for Biophotovoltaics Prepared by Expanding the Genetic Code, Sustainable Chemistry and Engineering, 2016, 72-77, American Chemical Society.
Randers-Eichhorn et al., On-Line Green Fluorescent Protein Sensor with LED Excitation, Biotechnology and Bioengineering, 1997, 921-926, vol. 55, No. 6, John Wiley & Sons Inc.
Panda et al., Porphyrins in bio-inspired transformations: Light-harvesting to solar cell, Coordination Chemistry Reviews, 2012, 2601-2627, Elsevier B.V.
Mohammadpour et al., Potential of light-harvesting of bacteriorhodopsin co-sensitized with green fluorescence protein: A new insight into bioenergy application, Biomass and Bioenergy, 2016, 35-38, Elsevier B.V.
Chirgwandi et al., Properties of a Biophotovoltaic Nanodevice, The Journal of Physical Chemistry, 2008, 18717-18721, American Chemical Society.
Choi et al., Rectified photocurrent of molecular photodiode consisting of cytochrome c/GFP hetero thin films, Biosensors & Bioelectronics, 2001, 819-825, Elsevier B.V.
Choi et al., Rectified photocurrent of the protein-based biophotodiode, Applied Physics Letters, 2001, 1570-1572, vol. 79, No. 10, American Institute of Physics.
Tulachan et al., The role of photo-electricproperties of silk cocoon membranein pupal metamorphosis: A natural solar cell, Scientific Reports, 2016.
Sharma, Aggregation and toxicity of titanium dioxide nanoparticles in aquatic environment, The Journal of Environmental Science and Health Part A, 2009, 1485-1495, Taylor & Francis Group LLC.
Trouiller et al., Titanium Dioxide Nanoparticles Induce DNA Damage and Genetic Instability In vivo in Mice, 2009, 8784-8789, American Association for Cancer Research.
Wiedenmann et al., Fluorescent Proteins for Live Cell Imaging: Opportunities Limitations and Challenges, 2009, 1029-1042.
Vegh et al., Chromophore Photoreduction in Red Fluorescent Proteins Is Responsible for Bleaching and Phototoxicity, The Journal of Physical Chemistry B, 2014, 4527-4534, American Chemical Society.
Lesser, Oxidative Stress Inmarine Environments: Biochemistry and Physiological Ecology, Annu. Rev. Physiol., 2006, 253-278, vol. 68, Annual Reviews.
Lacombe et al., Materials for selective photo-oxygenation vs. photocatalysis: preparation, properties and applications in environmental and health fields, Catalysis Science & Technology, 2016, 1571-1592, The Royal Society of Chemistry.
Saito et al., Mechanism of Singlet Oxygen Generation in Visible-Light-Induced Photocatalysis of Gold-Nanoparticle-Deposited Titanium Dioxide, The Journal of Physical Chemistry C, 2014, 15656-15663, American Chemical Society.
He et al., Unraveling the Enhanced Photocatalytic Activity and Phototoxicity of ZnO/Metal Hybrid Nanostructures from Generation of Reactive Oxygen Species and Charge Carriers, Applied Materials & Interfaces, 2014, 15527-15535, American Chemical Society.
He et al., Photogenerated Charge Carriers and Reactive Oxygen Species in ZnO/Au Hybrid Nanostructures with Enhanced Photocatalytic and Antibacterial Activity, Journal of the American Chemical Society, 2013, 750-757, American Chemical Society.
Hu et al., Singlet oxygen photogeneration and 2,4,6-TCP photodegradation at Pt/TiO2 under visible light illumination, RSC Advances, 2012, 12378-12383, The Royal Society of Chemistry.
Chen et al., Silk cocoon (*Bombyx mori*): Multi-layer structure and mechanical properties, Acta Biomaterialia, 2012, 2620-2627, Elsevier Ltd.
Hardy et al., Polymeric materials based on silk proteins, Polymer, 2008, 4309-4327, Elsevier Ltd.
Rockwood et al., Materials fabrication from Bombyx mori silk fibroin, Nature Protocols, 2011, 1612-1631, vol. 6, No. 10, Nature America Inc.
Wang et al., Effect of regeneration of liquid silk fibroin on its structure and characterization, Soft Matter, 2013, 138-145, The Royal Society of Chemistry.
Kim et al., Novel fabrication of fluorescent silk utilized in biotechnological and medical applications, Biomaterials, 2015, 48-56, Elsevier Ltd.

(56) References Cited

OTHER PUBLICATIONS

Toshiki et al., Germline transformation of the silkworm *Bombyx mori* L. using a piggyBac transposon-derived vector, Research Articles, 2000, 81-84, Nature America Ltd.

Teule et al., Silkworms transformed with chimeric silkworm/spider silk genes spin composite silk fibers with improved mechanical properties, PNAS, 2012, 923-928 vol. 109, No. 3.

Tansil et al., Functional Silk: Colored and Luminescent, Advanced Materials, 2012, 1388-1397, WILEY-VCH Verlag GmbH & Co. KGaA, Weinheim.

Iizuka et al., Colored Fluorescent Silk Made by Transgenic Silkworms, Advanced Functional Materials, 2013, 5232-5239, WILEY-VCH Verlag GmbH & Co. KGaA, Weinheim.

Pletnev, A Crystallographic Study of Bright Far-Red Fluorescent Protein mKate Reveals pH-induced cis-trans Isomerization of the Chromophore, The Journal of Biological Chemistry, 2008, 28980-28987, vol. 283, No. 43, JBC Papers in Press, U.S.A.

Pletnev et al., Structural Basis for Phototoxicity of the Genetically Encoded Photosensitizer KillerRed, The Journal ol Biological Chemistry, 2009, 32028-32039, LBC Papers in Press, U.S.A.

Pletneva, Crystal Structure of Phototoxic Orange Fluorescent Proteins with a Tryptophan- Based Chromophore, 2015, PloS One.

Stiel et al., 1.8 A bright-state structure of the reversibly switchable fluorescent protein Dronpa guides the generation of fast switching variants, Biochem. Journal, 2007, 35-42, Biochemical Society, Great Britain.

Evdokimov et al., Structural basis for the fast maturation of Arthropoda green fluorescent protein, EMBO Reports, 2006, 1006-1012, vol. 7, No. 10, European Molecular Biology Organization.

Chapagain et al., Fluorescent protein barrel fluctuations and oxygen diffusion pathways in mCherry, The Journal of Chemical Physics, 2011, 235101-1-235101-6, American Institute of Physics.

Yu et al., Laundering Durability of Photocatalyzed Self-Cleaning Cotton Fabric with TiO2 Nanoparticles Covalently Immobilized, Applied Materials & Interfaces, 2013, 3697-3703, American Chemical Society.

Foster et al., Photocatalytic disinfection using titanium dioxide: spectrum and mechanism of antimicrobial activity, Appl Microbiol Biotechnol, 2011, 1847-1868, Springer-Verlag.

Pelaez et al., A review on the visible light active titanium dioxide photocatalysts for environmental applications, Applied Catalysis B: Environmental, 2012, 331-349, Elsevier B.V.

Dudem et al., Hierarchical Ag/TiO2/Si Forest-Like Nano/Micro-Architectures as Antireflective, Plasmonic Photocatalytic, and Self-Cleaning Coatings, Sustainable Chemistry & Engineering, 2018, 1580-1591, American Chemical Society.

Choi et al., Molecular-scale biophotodiode consisting of a green fluorescent proteinÔcytochrome c self-assembled heterolayer, Applied Physics Letters, 2004, 2187-2189, vol. 84, American Institute of Physics.

Cohn et al., Comparison of fluorescence-based techniques for the quantification of particle-induced hydroxyl radicals, Particle and Fibre Toxicology, 2008, BioMed Central Ltd.

Göl et al., Investigation of photophysical, photochemical and bovine serum albumin binding properties of novel water-soluble zwitterionic zinc phthalocyanine complexes, Synthetic Metals, 2012, 605- 613, Elsevier B.V.

Patel et al., New di-l-oxidovanadium(V) complexes with NNO donor Schiff bases: Synthesis, crystal structures and electrochemical studies, Polyhedron, 2017, 102-109, Elsevier Ltd.

Franco et al., Glutathione Depletion Is Necessary for Apoptosis in Lymphoid Cells Independent of Reactive Oxygen Species Formation, The Journal of Biological Chemistry, 2007, 30452-30465, vol. 282, No. 42, ASBMB, USA.

Nagy et al., Thermal stability of chemically denatured green fluorescent protein (GFP) A preliminary study, Thermochimica Acta, 2004, 161-163, Elsevier B.V.

Alkaabi et al., Effect of pH on Thermaland Chemical-Induced Denaturation of GFP, Applied Chemistry and Biotechnology, 2005, 149-156, vol. 126 , Humana Press Inc.

Verkhusha et al., High Stability of Discosoma DsRed as Compared to Aequorea EGFP, Biochemistry, 2003, 7879-7884, American Chemical Society.

Reid et al., Chromophore Formation in Green Fluorescent Protein, Biochemistry, 1997, 6786-6791, American Chemical Society.

Roy et al., Diffusion pathways of oxygen species in the phototoxic fluorescent protein KillerRed, Photochemical & Photobiological Sciences, 2010, 1342-1350, The Royal Society of Chemistry and Owner Societies.

Stuchebrukhov A., Long-Distance Electron Tunneling in Proteins: A New Challenge for Time-Resolved Spectroscopy, Laser Physics, 125-138, vol. 20, No. 1, Pleiades Publishing Ltd.

Lambert et al., Quantum biology, Nature Physics, 2012, 10-18, vol. 9, Macmillan Publishers Limited.

Wurtzler et al., Selective Photocatalytic Disinfection by Coupling StrepMiniSog to the Antibody CatalyzedWater Oxidation Pathway, 2016, PLoS One.

Acharya et al., Photoinduced Chemistry in Fluorescent Proteins: Curse or Blessing?, Chemical Reviews, 2016, 758-795, American Chemical Society.

Wojtovich et al., Optogenetic control of ROS production, Redox Biology, 2014, 368-367, Elsevier B.V.

Subach et al., Chromophore Transformations in Red Fluorescent Proteins, Chemical Reviews, 2012, 4308-4327, American Chemical Society.

Shcherbo et al., Far-red fluorescent tags for protein imaging in living tissues, Biochem. Journal, 2009, 567-574, Biochemical Society.

Strack et al., A noncytotoxic DsRed variant for whole-cell labeling, Nature Methods, 2008, 955-957, vol. 5, No. 11, Mature Publishing Group.

Strack et al., A Rapidly Maturing Far-Red Derivative of DsRed-Express2 for Whole-Cell Labeling, Biochemistry Rapid Reports, 2009, 8279-8281, American Chemical Society.

Filonov et al., A Rapidly Maturing Far-Red Derivative of DsRed-Express2 for Whole-Cell Labeling, Nature Biotechnology, 2009, 757-776, vol. 29, No. 8, Nature America Inc.

Tour et al., Genetically targeted chromophore-assisted light inactivation, Nature Biotechnology, 2003, 1505-1508, vol. 21, No. 12, Nature Publishing Group.

Marelli et al., Silk Fibroin as Edible Coating for Perishable Food Preservation, Scientific Reports, 2016.

Sarkisyan et al., KillerOrange, a Genetically Encoded Photosensitizer Activated by Blue and Green Light, Novel Genetically Encoded Photosensitizer, 2015, PLoS One.

Wojtovich et al., Chromophore-Assisted Light Inactivation of Mitochondrial Electron Transport Chain Complex II in Caenorhabditis elegans, Scientific Reports, 2016.

Pryor, Oxy-Radicals and Related Species: Their Formation, Lifetimes, and Reactions, 1986, 657-667, Annual Reviews Inc.

Winterbourn, Reconciling the chemistry and biology of reactive oxygen species, Nature Chemical Biology, 2008, 278-286, Nature Publishing Group.

Baptista et al., Type I and Type II Photosensitized Oxidation Reactions: Guidelines and Mechanistic Pathways, Photochemistry and Photobiology, 2017, 912-919, The American Society of Photobiology.

Greenbaum et al., Green Fluorescent Protein Photobleaching: a Model for Protein Damage by Endogenous and Exogenous Singlet Oxygen, Biol. Chem., 2000, 1251-1258, vol. 381, Walter de Gruyter.

Jimenez-Banzo et al., Singlet oxygen photosensitisation by GFP mutants: oxygen accessibility to the chromophore, Photochemical & Photobiological Sciences, 2010, 1336-1341, The Royal Chemistry Society and Owner Societies.

Vegh et al., Reactive oxygen species in photochemistry of the red fluorescent protein "Killer Red", ChemComm., 2011, 4887-4889, The Royal Society of Chemistry.

Ogibly, Singlet oxygen: there is indeed something new under the sun, Chemical Society Reviews, 2010, 3181-3209, The Royal Society of Chemistry.

(56) References Cited

OTHER PUBLICATIONS

Schweitzer et al., Physical Mechanisms of Generation and Deactivation of Singlet Oxygen, Chem. Rev., 2003, 1685-1757, American Chemical Society.

* cited by examiner

| No | Location | Mr(exp) | Mr(calc) | Sequence |
|---|---|---|---|---|
| 1 | 49-63 | 1590.8493 | 1589.8148 | DASGAVIEEQITTKK |
| 2 | 70-79 | 2442.8413 | 2441.1519 | NHGILGKNEK |
| 3 | 83-104 | 2442.8413 | 2441.1519 | TFVITTDSDGNESIVEEDVLMK |
| 4 | 159-171 | 1637.3093 | 1637.7462 | MVSELIKENMHMK |
| 5 | 172-184 | 1589.3663 | 1589.7296 | LYMEGTVNNHHFK |
| 6 | 185-201 | 1946.4763 | 1945.8145 | CTSEGEGKPYEGTQTMR |
| 7 | 204-226 | 2433.9883 | 2433.1925 | AVEGGPLPFAFDILATSFMYGSK |
| 8 | 252-279 | 3062.0203 | 3060.4597 | VTTYEDGGVLTATQDTSLQDGCLIYNVK |
| 9 | 280-294 | 1660.4443 | 1660.8242 | IRGVNFPSNGPVMQK |
| 10 | 295-316 | 2350.9313 | 2351.1440 | KTLGWEASTETLYPADGGLEGR |
| 11 | 348-357 | 1270.9383 | 1270.6128 | MPGVYVVDRR |
| 12 | 363-379 | 1973.5673 | 1973.9330 | EADKETYVEQHEVAVAR |
| 13 | 380-386 | 881.6313 | 881.3953 | YCDLPSK |
| 14 | 387-403 | 1826.5823 | 1827.8863 | LGHRPQQVDSVSYGAGR |
| 15 | 404-422 | 1687.4983 | 1685.7604 | GYGQGAGSAASSVSSASSR |
| 16 | 423-429 | 945.4853 | 945.4304 | SYDYSRR |
| 17 | 433-439 | 843.3973 | 843.4385 | KNCGIPR |

FIG. 8

FLUORESCENT PROTEIN ACTIVATED SILK USED IN PHOTOELECTRIC CONVERSION

CROSS-REFERENCE TO RELATED APPLICATIONS

The present patent application is related to and claims the priority benefit of U.S. Provisional Patent Application Ser. No. 62/448,332, filed Jan. 19, 2017, and U.S. Provisional Patent Application Ser. No. 62/593,976, filed Dec. 3, 2017, the contents of each of which is hereby incorporated by reference in its entirety into the present disclosure. The present patent application is concurrently filed with a companion application entitled "Light Activated Photoreaction Via Genetic Hybridization of Far-Red Fluorescent Protein and Silk" the contents of which is hereby incorporated into the present disclosure in its entirety.

STATEMENT REGARDING GOVERNMENT FUNDING

This invention was made with government support under FA2386-16-1-4114 awarded by US Air Force Office of Scientific Research and FA2386-17-1-4072 awarded by US Air Force Office of Scientific Research. The government has certain rights in the invention.

SEQUENCE LISTING

This application contains a Sequence Listing which has been submitted as sequence listing text file "PRF-67206-05_ST25.txt", file size of 6.4 KB, created on Mar. 2, 2018. The aforementioned sequence listing is hereby incorporated by reference in its entirety.

TECHNICAL FIELD

The present disclosure generally relates to photo-electrical conversion, and in particular to a class of devices that utilize protein activated silk as the conversion material.

BACKGROUND

This section introduces aspects that may help facilitate a better understanding of the disclosure. Accordingly, these statements are to be read in this light and are not to be understood as admissions about what is or is not prior art.

There are several different photovoltaics technologies, including semiconductor-based crystalline and thin-film solar cells, perovskite solar cells, and dye-sensitized solar cells (DSSC).

A conventional semiconductor-based light-to-electricity converter cell (a photovoltaic cell) includes a first p-type semiconductor layer with a first-type (anode) conductivity and a second n-type semiconductor layer with a second-type (cathode) conductivity opposite the first-type that are separated by a buffer layer. A first electrode is connected to the first semiconductor layer and a second electrode connected to the second semiconductor layer, where light can be applied to the first semiconductor layer and thereby generate electron-hole pairs and which migrate to a corresponding of the first and second layers, thereby generating a potential difference between the first and second electrodes. To this end, photovoltaic elements convert light to electrical energy. This property is used in solar cell arrays as well as photodetector. Solar cells and photodetectors are now ubiquitous. Solar cell arrays have gained particular interest as they promise to provide unlimited amount of energy from sunlight.

As explained above, a conventional solar cell includes a p-type semiconductor and an n-type semiconductor, and when solar energy is absorbed at a photoactive layer, an electron-hole pair is generated, the generated electrons and holes move to the n-type semiconductor and the p-type semiconductor respectively, and are collected by electrodes, which can generate electrical energy.

While perhaps less polluting than other energy-generating schemes such as coal-operated powerplants, recycling traditional solar cells and photodetectors can be cumbersome and dispensing of them at large quantities in landfills can lead to environmental challenges. Furthermore, the cost of manufacturing these cells at high volumes for the stated purposes and other purposes can be a limiting factor for their widespread availability. Furthermore, use of photodetectors inside human body for various applications, such as imaging, has been challenging since conventional photodetectors are not biocompatible.

One solution to reduce eco-friendliness of solar cells is in the development of a new area called dye-sensitized solar cells (DSSC). A DSSC includes an anode and a cathode. The anode includes a transparent substrate or cover plate which is typically coated with a transparent conductive oxide (TCO) film such as indium tin oxide (ITO). A layer of titanium dioxide ($TiO_2$), a somewhat biocompatible/biodegradable material with semiconductor properties is then applied to the film. A layer of dye (also called a photosynthesizer) is then placed on the $TiO_2$ layer. An electrolyte is used in between the anode and a cathode. The electrolyte is typically an iodide/triiodide solution ($I^-/I_3^-$). The cathode is another metal (e.g. platinum) or carbon-based catalyst coated on a TCO substrate or cover plate. When light shines on the DSSC, dye molecules become excited and are energized from their normal ground state to a higher energy level. The dye molecule thus becomes oxidized and a free electron is thus injected into the conduction band of the semiconductor material (i.e. $TiO_2$), thereby allowing a potential at the anode where it is collected for powering a load. The electrolyte donates an electron to the oxidized dye molecule to regenerate the molecule by receiving an electron from the cathode, thus creating a current when the anode and cathode are connected in an external circuit.

However, the dye in the DCCS can be non-biocompatible or non-biodegradable. In certain cases, the commonly used dye can have toxicity and is a carcinogen. As a result, implementation of a photodetector based on this concept inside a biological system can become challenging.

Therefore, there is an unmet need for a novel approach that can convert photonic energy to electrical energy and which is friendly to the environment and is biocompatible. The recent advances in wearable and flexible electronics and biosensors have mandated the co-development of new types of biocompatible biotic solar cells.

The power-conversion efficiency of a photovoltaic device can be enhanced by improving light coupling between free space (air) and the device. Oftentimes, an essential design of light coupling processes of incident solar light has not been considered. In this respect, light localization (or light confinement) can be implemented to enhance the light coupling. In particular, strong light localization in disordered or irregular structures can result in light localization on broad spectral and angular ranges.

SUMMARY

A biotic photoelectric device is disclosed. The photoelectric device includes a first electrode, a second electrode, and an electrolyte disposed between the first electrode and the second electrode. The second electrode includes a transparent layer for allowing light to penetrate into the second electrode, an electron transport layer coupled to the transparent layer, and a genetically hybridized fluorescent silk layer as a protein photo-sensitizer coupled to the electron transport layer.

BRIEF DESCRIPTION OF DRAWINGS

FIGS. 8 and 9 are sequence listings for peptides from mKate2 and sequence alignment of mKate2/Fibroin H-chain fusion recombinant protein amino acid.

DETAILED DESCRIPTION

Figure 1:
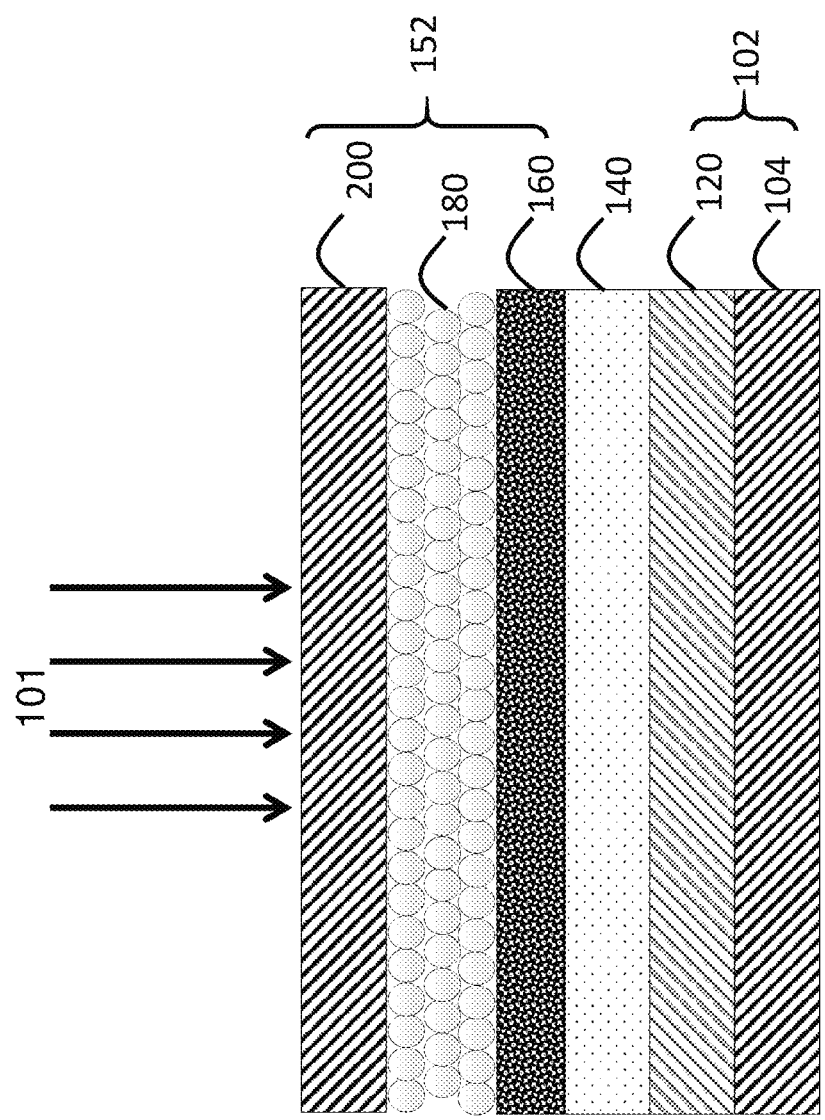
FIG. 1 is a cross sectional representation of a device according to the present disclosure.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In the present disclosure, the term "about" can allow for a degree of variability in a value or range, for example, within 10%, within 5%, or within 1% of a stated value or of a stated limit of a range.

In the present disclosure, the term "substantially" can allow for a degree of variability in a value or range, for example, within 90%, within 95%, or within 99% of a stated value or of a stated limit of a range.

A novel arrangement for converting photonic energy to electrical energy is presented which is friendly to the environment and is biocompatible. Visible light-driven photocatalysis using plasmonics, which relies on the combination of semiconductor photocatalysts with metal nanostructures/nanoparticles, has received consideration attention for solar energy utilization and conversion. Solar photocatalysis has a variety of energy and environmental applications, such as hydrogen generation, carbon dioxide reduction, desalination, disinfection, and water/air purification. However, such approaches are often intrinsically limited for large-scale and mass production. In addition, potentially hazardous and adverse (e.g. carcinogenic and cytotoxic) effects associated with dye material in the dye sensitized solar cells (DSSC), discussed above, have limited widespread utilization for environmental remediation as well as biocompatibility and biodegradability. In this respect, the present disclosure describes utilization of plasmonic photocatalyst-like biological materials in the form of hybridized protein transgenic silk and further translate them into industrially relevant production.

Referring to FIG. 1, a cross sectional view of a device 100 (not drawn to scale) according to the present disclosure is presented. The device 100 includes a first electrode 102 (an anode) which includes a conductive layer 104 and a platinum (Pt) layer 120 (a cathode) atop the conductive layer 104. The conductive layer 104 typically may optionally include a layer of transparent conductive oxide (TCO) such as Indium tin oxide (ITO) or fluorine doped tin oxide (FTO). An electrolyte (e.g., iodide/triiodide solution) 140 is in contact with the first electrode 102. The electrolyte 140 is disposed between the first electrode 102 and a second electrode 152 (an anode) which includes a layer of hybridized protein transgenic silk 160, a layer of an electron transport layer 180 (TiO$_2$) with bandgap characteristics that allows energized electrons to move from the higher level of proteins to the conduction band of electron transport layer 180, and a conductive layer 200. The electron transport layer 180 can be an ecologically and biologically friendly material such as TiO$_2$. The conductive layer 200 typically includes a layer of TCO such as ITO or fluorine doped tin oxide (FTO).

Figure 2:
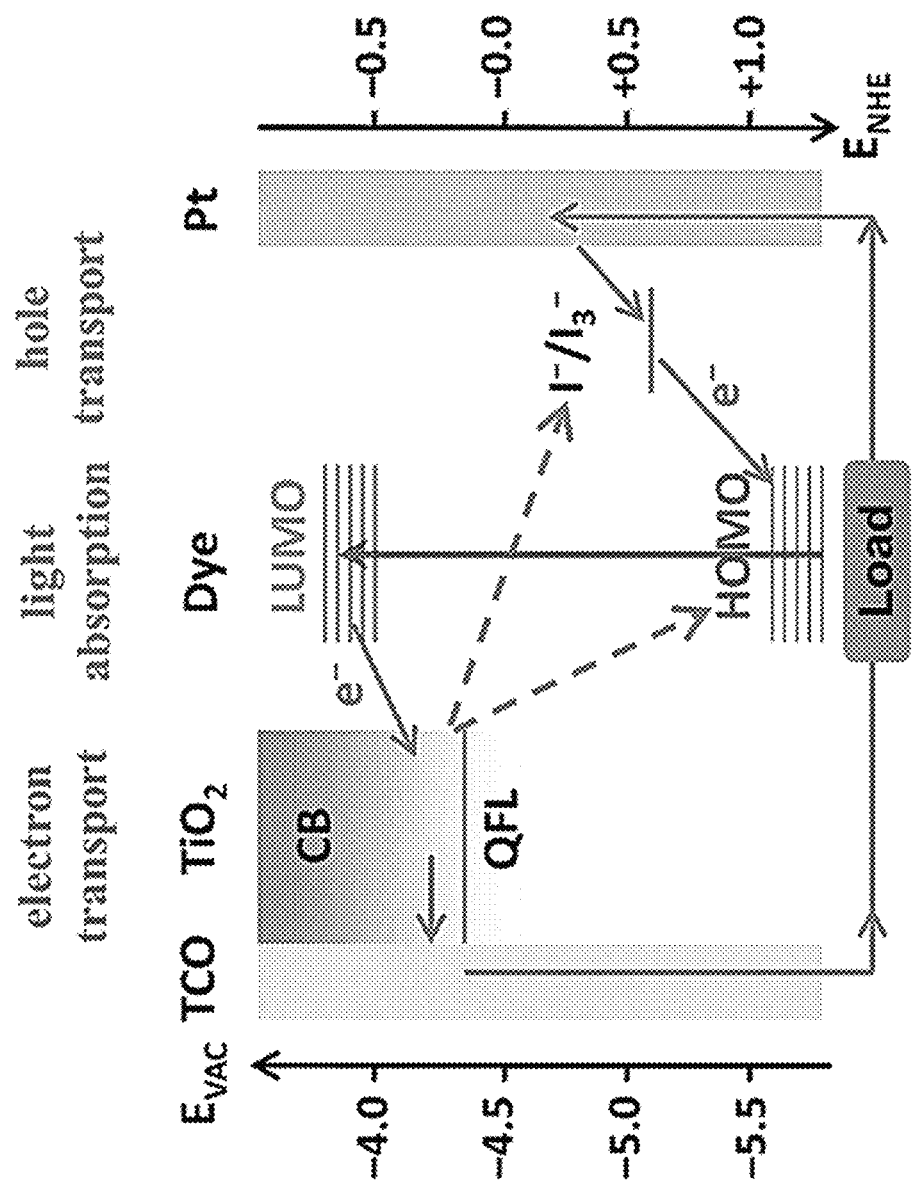
FIG. 2 is an energy diagram showing electron transport mechanism, based on the device of FIG. 1.
Figure 3:
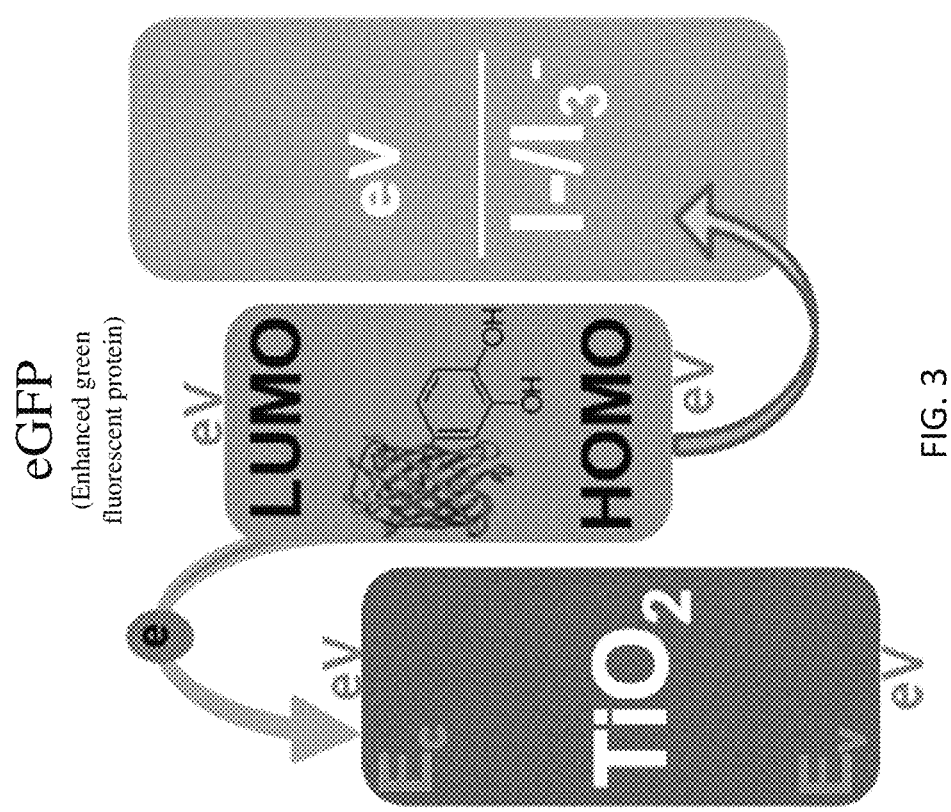
FIG. 3 is another schematic showing electron transport based on the device of FIG. 1.

When light 101 is shown on the second electrode 152, the fluorescent protein in the layer of hybridized protein transgenic silk 160 becomes energized from their normal ground state to a higher energy level. The molecule of the fluorescent protein in the layer of hybridized protein transgenic silk 160 thus becomes oxidized and a freed electron is thus injected into the conduction band of the electron transport layer 180, thereby allowing a potential at the second electrode 152, where it is collected for powering a load. The electrolyte 140 then donates electrons to the oxidized molecules of the fluorescent protein in the layer of hybridized protein transgenic silk 160 to regenerate the molecules by receiving an electron from the first electrode 102 thus, creating a current when the second electrode 152 (anode) the first electrode 102 (cathode) are connected in a circuit (not shown). The above-described electron-hole generation is depicted in further detail in FIGS. 2 and 3. In particular, when the fluorescent protein molecules in the layer of hybridized protein transgenic silk 160 are irradiated, the molecules are energized from their ground state (i.e., highest occupied molecular orbit—HOMO—to a higher energy state (i.e., lowest unoccupied molecular orbit—LUMO—S*, as described in equation 1 below:

$$S \rightarrow S^*, \qquad (1)$$

where S represents the HOMO energy level, and S* represents the LUMO energy level. The fluorescent protein molecules in the layer of hybridized protein transgenic silk 160 then become oxidized and in doing so release an electron which now has sufficient energy to move from the valence band to the conduction band, as described in equation 2, below:

$$S^* \rightarrow S^+ + e^-, \quad (2)$$

where $S^+$ is the oxidized molecule, and
$e^-$ is the energized electron in the conduction band (CB) of the electron transport layer 180. The oxidized dye molecule ($S^+$) is regenerated by electrons donated from the electrolyte of the electrolyte later 140 ($I^-/I_3^-$), as shown in equation 3, below:

$$S^+ + 3/2 I^- \rightarrow S + \frac{1}{2} I_3^-, \quad (3)$$

The electrolyte of the electrolyte layer 140 is then regenerated by donation of electrons from the second electrode 102 (cathode), as described by equation 4, below:

$$\frac{1}{2} I_3^- + e^- \rightarrow 3/2 I^- \quad (4)$$

According to the present disclosure, biological hybridization of far-red fluorescent proteins and some natural proteins (i.e. silk) is disclosed for a new class of genetically encoded photosensitization activated using visible (or solar) light, directly producing selective radical species. As an example, transgenic red fluorescent proteins (RFP) silk can be mass-produced by scalable and continuous manufacturing. Using the polymeric nature of silk, transgenic RFP silk can also be processed into nanomaterials and nanostructures in a variety of forms.

Figure 4:
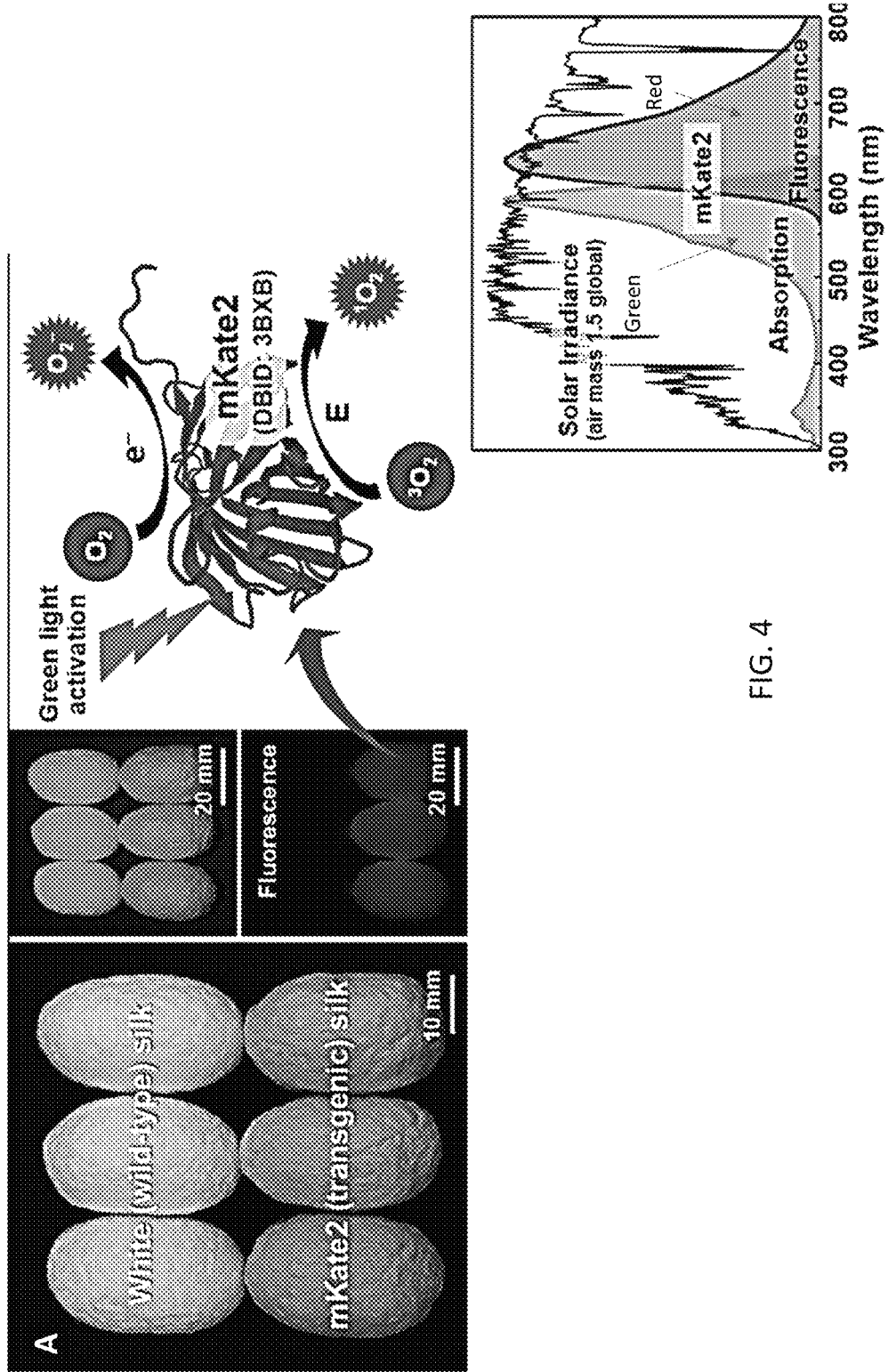
FIG. 4 is a schematic illustration of reactive oxygen species (ROS) generating mKate2 (transgenic) silk cocoons vs. white (wild-type) silk cocoons both under white light and under green light activation.

Silk produced by silkworms has extensively been utilized as fabrics and processed into engineered biomaterials due to its various merits of the superior mechanical and optical properties as well as the biocompatibility and biodegradability. According to the present disclosure, genetically engineered domesticated silkworms are used to generate the biomaterial of interest. The transgenes of interests are expressed by germline transformation using the gene splicing method piggyBac, known to a person having ordinary skill in the art. This silkworm transgenesis method yields transformed animals for multiple successive generations and produces recombinant substances in large amounts. Silkworm transgenesis readily produces natural photocatalyst and photosensitizer materials in an eco-friendly manner, minimizing the use of industrial facilities. Regarding ecological hazard, transgenic silkworms are highly unlikely to pose threats to natural ecosystems, because silkworms are dependent on humans for survival and reproduction as a completely domesticated indoor insect.

mKate2, which is a far-red monomeric fluorescent protein, was chosen as one of the transgenic RFP silk. Referring to FIG. 4, a schematic illustration of ROS generating mKate2 (transgenic) silk cocoons vs. white (wild-type) silk cocoons is shown both under white light and under green light activation. When light shines on mKate2 silk, dye molecules become excited from their ground state to a higher energy state, thereby releasing electrons. Oxygen molecules in presence of free electrons go through a reductive reaction ($O_2 \rightarrow O_2^-$) thereby generating reactive oxygen species (ROS) of superoxide ($O_2^-$) radical and singlet molecular oxygen ($^1O_2$), as shown in FIG. 4. Also shown in FIG. 4 is a spectral output showing mKate2 energy as a function of light wavelength in nm. The AM 1.5 Standard spectrum refers to a standard terrestrial solar spectrum. The green and the red curves presents the absorption spectrum and the fluorescent emission spectrum of mKate2. Thus, mKate2 can be activated by solar light.

Figure 5:
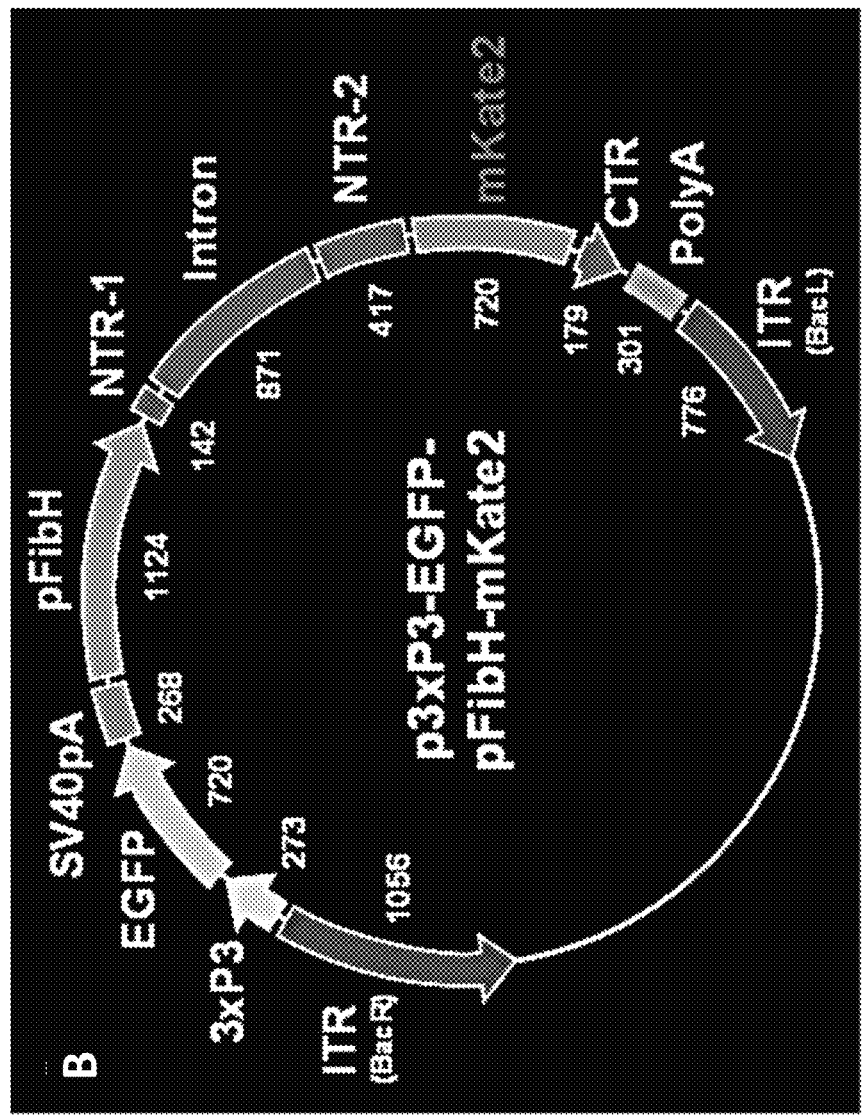
FIG. 5 is a schematic representing construction of transfer vector p3×P3-EGFP-pFibH-mKate2 for mKate2 silkworm transgenesis.
Figure 6:
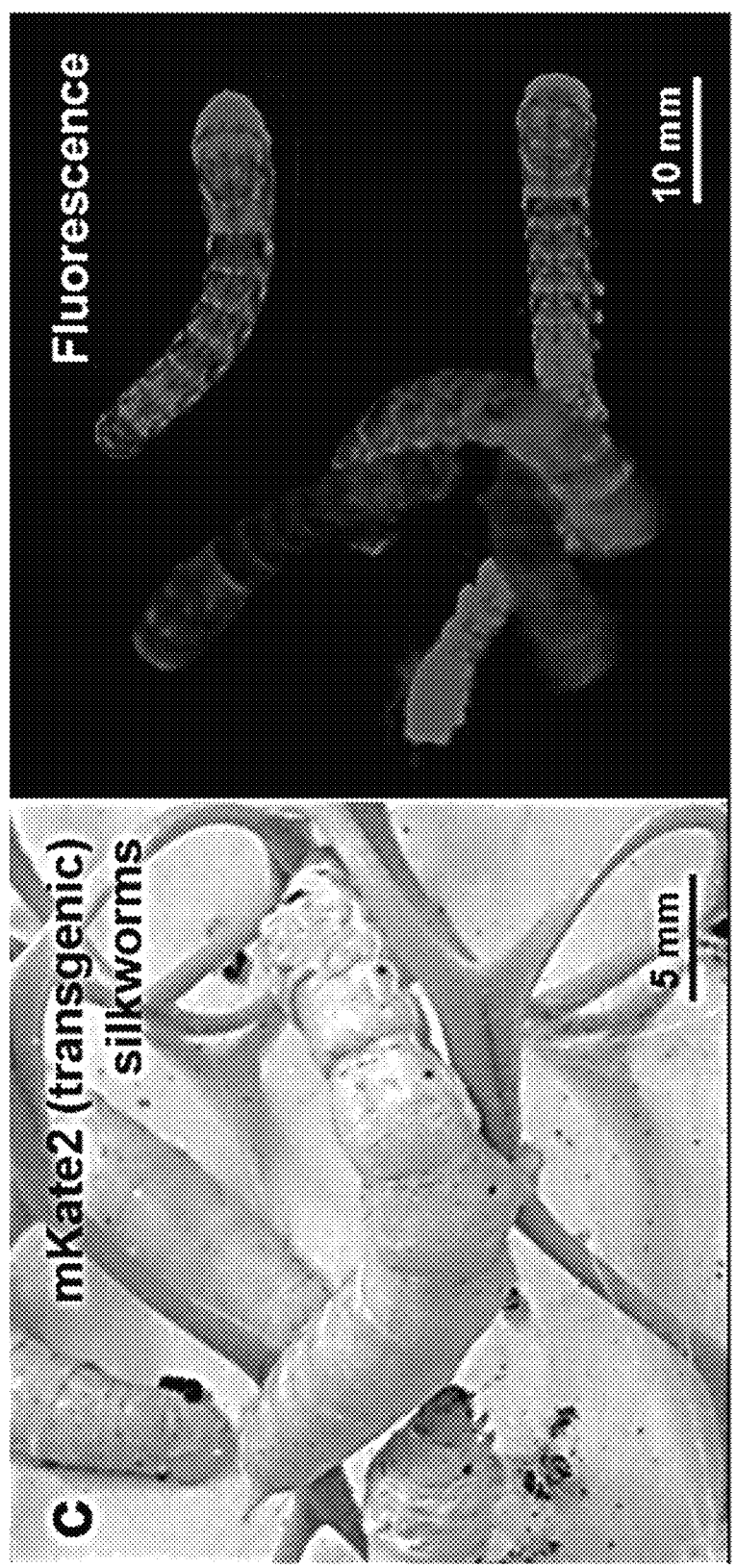
FIG. 6 is a photograph (left) and fluorescent image (right) of the silk gland for the transgenic mKate2 silkworm larvae at the 3rd day of the 5th instar.
Figure 7:
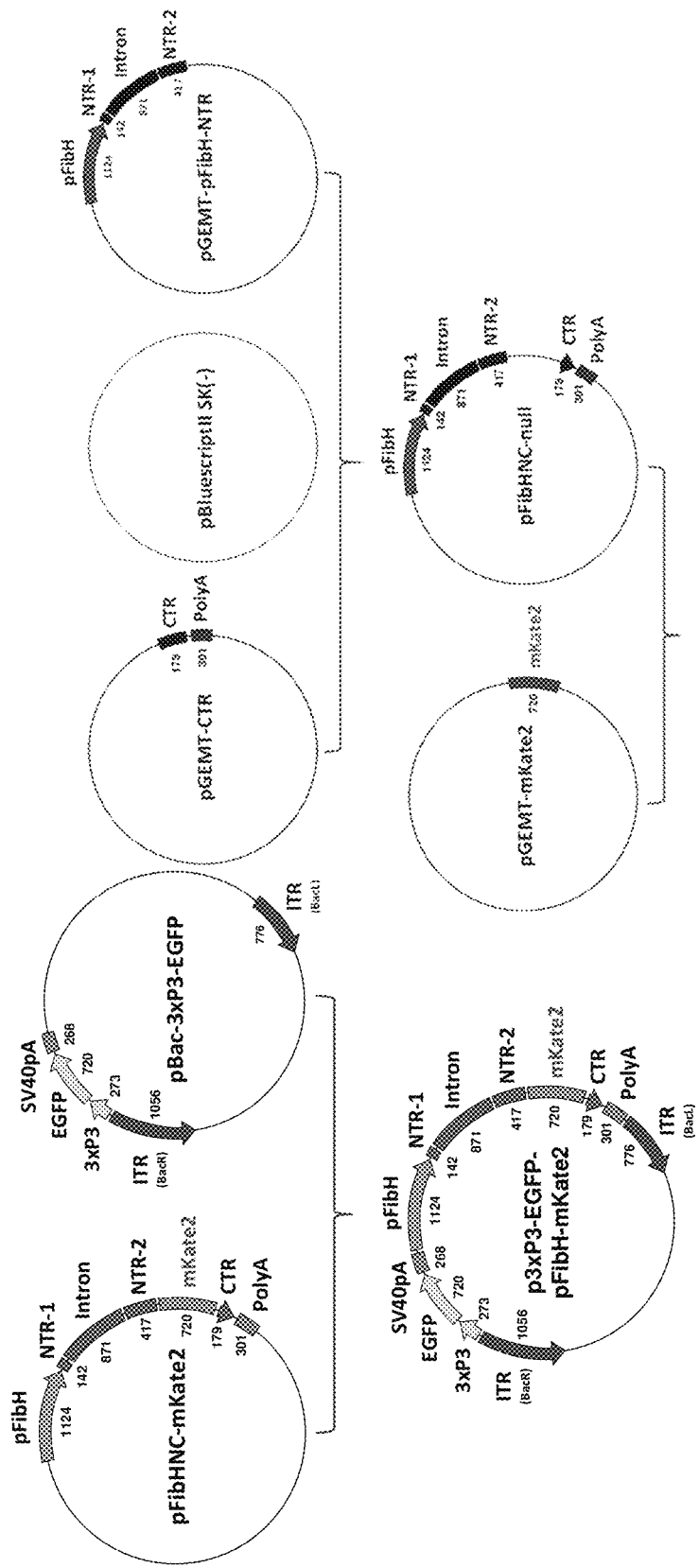
FIG. 7 is a schematic showing a nucleotide sequences of pFibH-NTR and CTR derived from Genebank Accession No. AF226688. pFibH: fibroin heavy chain promoter domain (1124 bp), NTR-1: N-terminal region 1 (142 bp), intron: first intron (871 bp), NTR-2: N-terminal region 2 (417 bp), CTR: Cterminal region (179 bp), PolyA: poly(A) signal region (301 bp), EGFP: enhanced green fluorescent protein gene, mKate2: monomeric far-red fluorescent protein, ITR (BacR, BacL): inverted repeat sequences of piggyBac arms, 3×P3: 3×P3 promoter, and SV40: SV40 polyadenylation signal sequence.

Referring to FIG. 5, a schematic representing construction of transfer vector p3×P3-EGFP-pFibH-mKate2 for mKate2 silkworm transgenesis is shown. For hybridization of mKate2 and silk, mKate2 gene is fused with N-terminal and C-terminal domains of the fibroin heavy chain promoter (pFibH); p3×P3-EGFP-pFibH-mKate2 is the constructed transformation vector Referring to FIG. 7, a schematic is provided showing a nucleotide sequences of pFibH-NTR and CTR are derived from Genebank Accession No. AF226688. pFibH: fibroin heavy chain promoter domain (1124 bp), NTR-1: N-terminal region 1 (142 bp), intron: first intron (871 bp), NTR-2: N-terminal region 2 (417 bp), CTR: Cterminal region (179 bp), PolyA: poly(A) signal region (301 bp), EGFP: enhanced green fluorescent protein gene, mKate2: monomeric far-red fluorescent protein, ITR (BacR, BacL): inverted repeat sequences of piggyBac arms, 3×P3: 3×P3 promoter, and SV40: SV40 polyadenylation signal sequence. 3×P3-EGFP is only for screening a large number of G1 broods, because EGFP fluorescent signals are easily monitored in the stemmata and nervous system at early embryonic and larval stages. Referring to FIG. 6, a photograph (left) and a fluorescent image (right) of the silk gland for the transgenic mKate2 silkworm larvae at the 3rd day of the 5th instar. The silk gland of genetically-encoded mKate2 silkworms is fluorescent.

Figure 9:
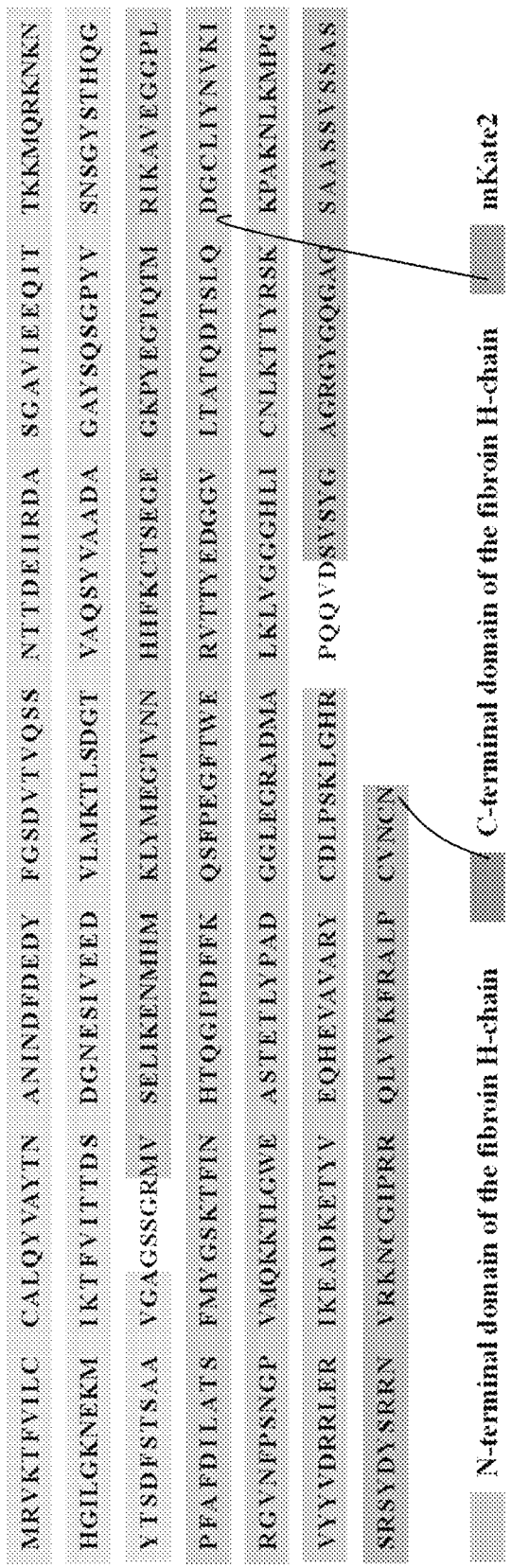

The homogenous production of mKate2 silk results in a mass density of ~12.6% mKate2/Fibroin H-chain fusion recombinant protein. In FIG. 4, white (wild-type) silk cocoons are not fluorescent, while mKate2-expressing silk cocoons are fluorescent at excitation of $\lambda_{ex}$=543 nm. Referring to FIGS. 8 and 9, shown are sequence listings for peptides from mKate2 and sequence alignment of mKate2/Fibroin H-chain fusion recombinant protein amino acid. The surface morphologies of silk cocoons were imaged using a scanning electron microscopy (SEM) system (FEI Quanta 3D FEG; Oregon, USA) at 10 keV. In exploiting the fluorescence emission of mKate2 silk, we also performed confocal imaging using an Olympus Fluoview FV1000 confocal laser scanning system adapted to an Olympus IX81 inverted microscope with a 20× UPlanSApo water immersion objective (Olympus, Tokyo, Japan). A green laser excitation source ($\lambda_{ex}$=543 nm) was used with a detection bandpass of 600-700 nm. The typical configuration of confocal microscopy can be summarized as follows: confocal aperture size=50 μm (i.e. ~0.5 airy unit), NA=0.4, and scan speed (pixel dwell time)=10 μs/pixel. 43 image slices were stacked with a slice thickness of 5 μm along the z-axis, covering an area up to ~1270×1270 μm². The three-dimensional (3D) stacked image was also visualized using Imaris 5.0.

Figure 10:
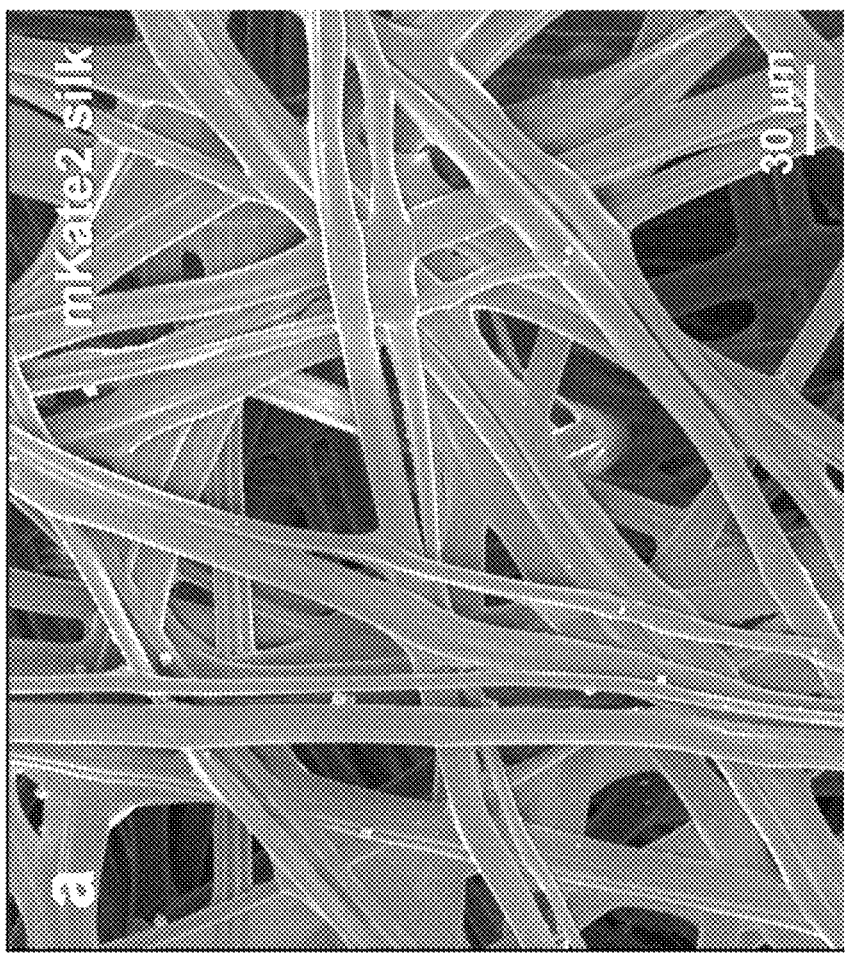
FIGS. 10, 11, and 12 include an SEM image of mKate2 silk fibers (FIG. 10); and confocal fluorescence microscopy images of mKate2 silk fibers under green light excitation (FIGS. 11 and 12).
Figure 11:
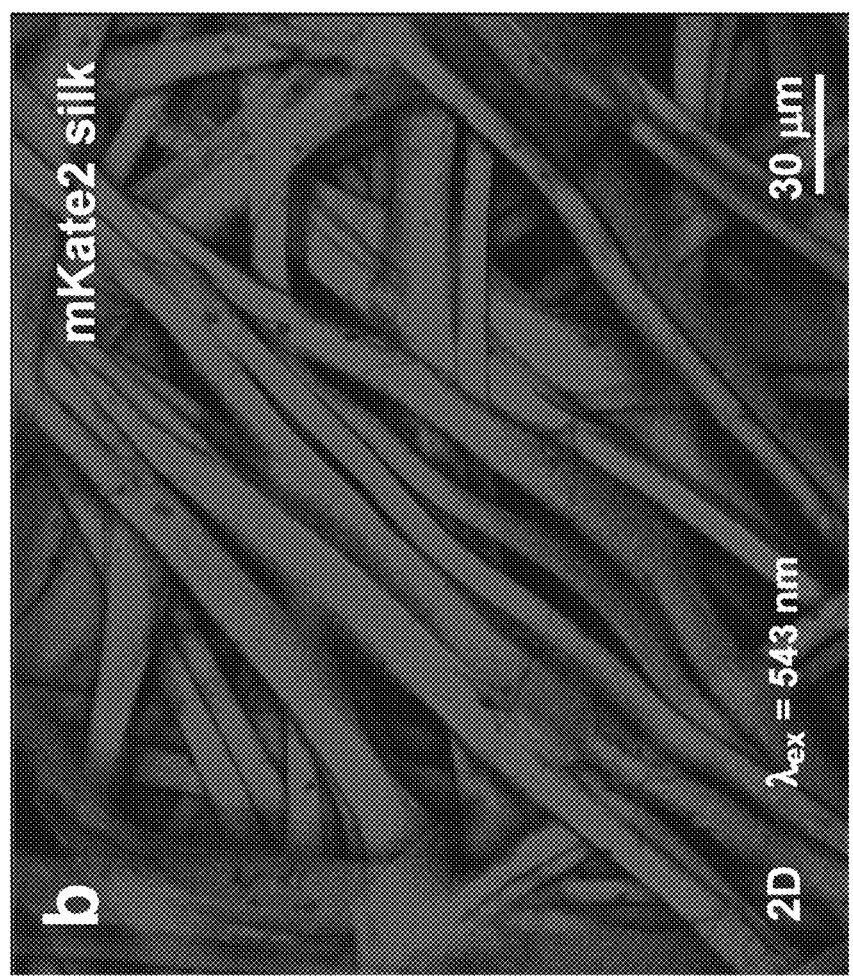
Figure 12:
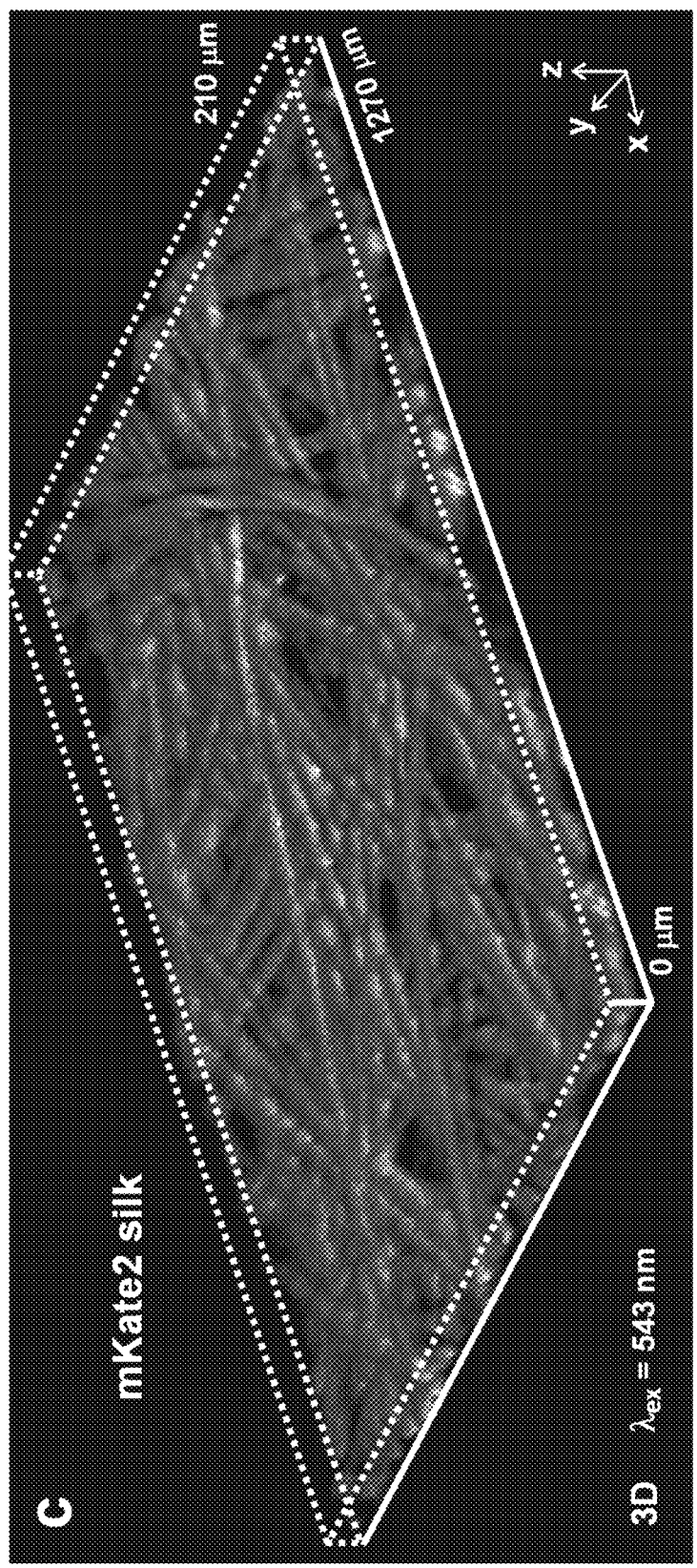

Referring to FIGS. 10, 11, and 12, an SEM image of mKate2 silk fibers (FIG. 10); confocal fluorescence microscopy images of mKate2 silk fibers under green light excitation (FIGS. 11 and 12), are provided. Mass density of mKate2/Fibroin H-chain fusion recombinant protein in the transgenic mKate2 silk is estimated to be ~12.6%.

Figure 13:
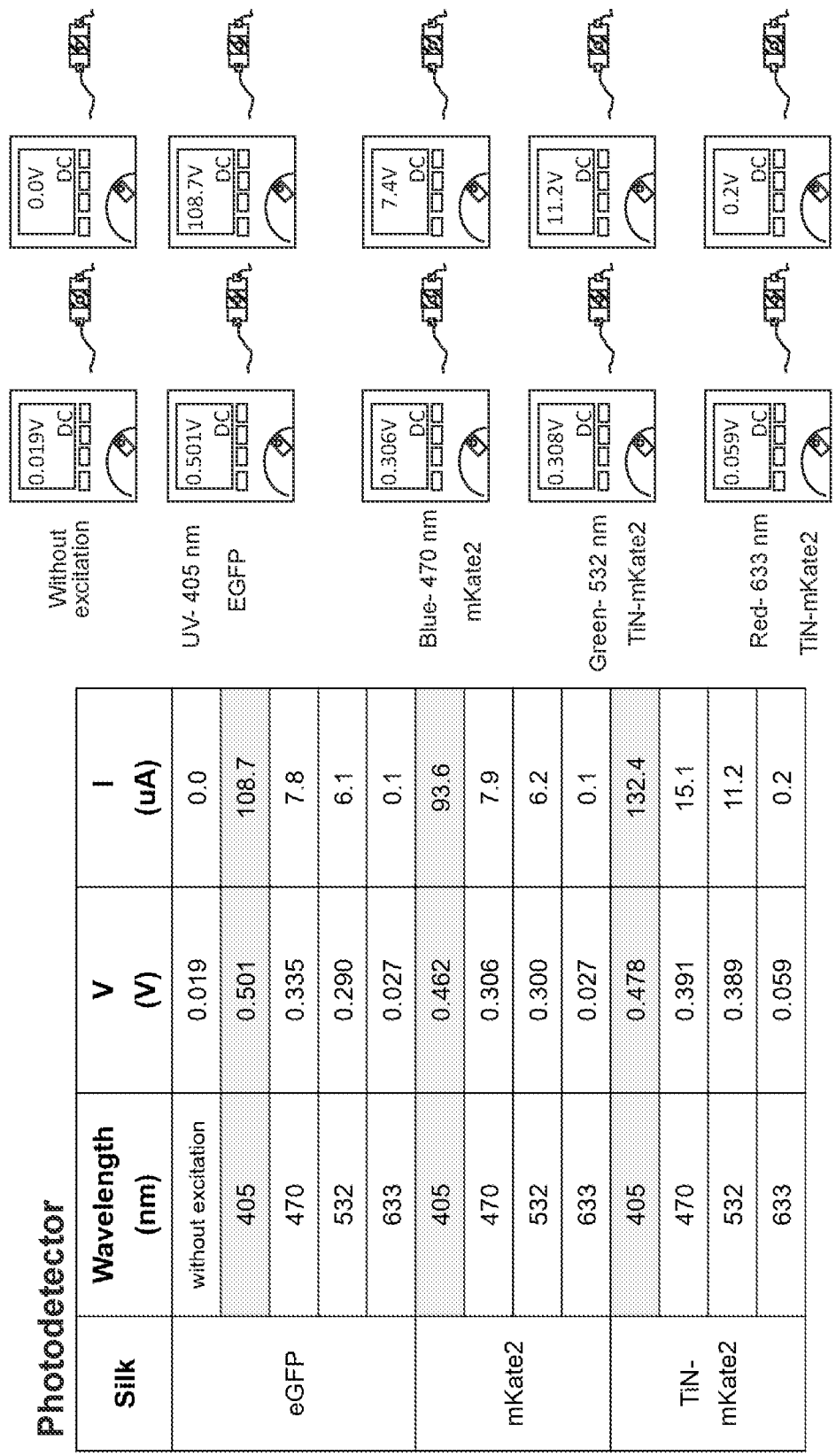
FIG. 13 is a set of photographs and a table showing the results of electrical measurements based on different types of transgenic proteins in silk.

A similar mechanism is followed in a solar cell application or a photodetector application of the device 100 of FIG. 1. Three different hybridized protein transgenic silk materials were developed. First is eGFP (Enhanced green fluorescent protein) is chosen as the transgenic protein. According to another embodiment, mKate2 is chosen as the transgenic protein. Finally, TiN mKate2 is chosen as the transgenic protein. The result of different irradiation vs. voltage and current generated for these various transgenic proteins is shown in FIG. 13. At 405 nm, the highest V and I values are obtained for TiN mKate2. This may be attributed to the light absorption (<430 nm) of the electrolyte ($I^-/I_3^-$, iodide/triiodide electrolyte of the electrolyte layer 160).

To obtain the TiN-hybrid transgenic silk, we fed TiN nanopowders to transgenic silkworms. Titanium nitride (TiN) is a hard material with gold-like optical properties, which is commonly used as coatings for various substrates due to its high melting temperature, strong corrosion resistance, and non-toxicity/biocompatibility.

It should also be appreciated that light can be localized in natural silk (silk fibers and silk cocoons) in the same manner of Nobel Prize winner Philip Anderson's theory (also known as Anderson localization). Anderson light localization in irregular or disordered structures allows for light confinement (or trapping) on broad spectral and angular ranges. Thus, natural silk can offer a robust platform for high-efficiency photovoltaic devices. Anderson light localization of silk enhances light coupling between free space and the photoelectric device on broad spectral and substantially all angular ranges.

Those having ordinary skill in the art will recognize that numerous modifications can be made to the specific implementations described above. The implementations should not be limited to the particular limitations described. Other implementations may be possible.

The invention claimed is:

1. A photoelectric device, comprising:
a first electrically conductive electrode;
a second electrically conductive electrode; and
an electrolyte disposed between the first electrode and the second electrode,
the second electrode including
a transparent layer for allowing light to penetrate into the second electrode,
an electron transport layer coupled to the transparent layer, and
a genetically hybridized fluorescent silk layer coupled to the electron transport layer.

2. The photoelectric device of claim 1, wherein the genetically hybridized fluorescent silk is generated from genetically engineered domesticated silkworms (*Bombyx mori*), wherein Anderson light localization of silk enhances light coupling between free space and the photoelectric device on broad spectral and angular ranges.

3. The photoelectric device of claim 2, wherein the genetically hybridized fluorescent silk is enhanced green fluorescent protein (eGFP) silk.

4. The photoelectric device of claim 3, wherein the output of the photoelectric device ranges from about 0.5 V to about 0.027 V as a function of irradiation wavelength ranging from about 405 nm to about 633 nm, respectively.

5. The photoelectric device of claim 3, wherein the output of the photoelectric device ranges from about 109 µA to about 0.1 µA as a function of irradiation wavelength ranging from about 405 nm to about 633 nm, respectively.

6. The photoelectric device of claim 2, wherein the genetically hybridized fluorescent silk is mKate2 silk.

7. The photoelectric device of claim 6, wherein the output of the photoelectric device ranges from about 0.462 V to about 0.027 V as a function of irradiation wavelength ranging from about 405 nm to about 633 nm, respectively.

8. The photoelectric device of claim 6, wherein the output of the photoelectric device ranges from about 93.6 µA to about 0.1 µA as a function of irradiation wavelength ranging from about 405 nm to about 633 nm, respectively.

9. The photoelectric device of claim 2, wherein the genetically hybridized fluorescent silk is TiN mKate2 silk.

10. The photoelectric device of claim 9, wherein the output of the photoelectric device ranges from about 0.478 V to about 0.059 V as a function of irradiation wavelength ranging from about 405 nm to about 633 nm, respectively.

11. The photoelectric device of claim 9, wherein the output of the photoelectric device ranges from about 132.4 µA to about 0.2 µA as a function of irradiation wavelength ranging from about 405 nm to about 633 nm, respectively.

12. The photoelectric device of claim 1, wherein the photoelectric device is a solar cell.

13. The photoelectric device of claim 12, wherein a plurality of photoelectric devices are connected in a series manner to generate a voltage multiple.

14. The photoelectric device of claim 13, wherein the first electrode of one photoelectric device of the plurality is coupled to the second electrode of a neighboring photoelectric device of the plurality.

15. The photoelectric device of claim 12, wherein a plurality of photoelectric devices are connected in a parallel manner to generate a current multiple.

16. The photoelectric device of claim 13, wherein the first electrodes of the photoelectric devices of the plurality are coupled to each other and the second electrodes the photoelectric devices of the plurality are coupled to each other.

17. The photoelectric device of claim 1, wherein the photoelectric device is a photodetector.

18. The photoelectric device of claim 1, the transparent layer of the second electrode includes a layer of conductive oxide (TCO).

19. The photoelectric device of claim 18, the TCO layer includes one of Indium tin oxide (ITO), fluorine doped tin oxide (FTO), or a combination thereof.

20. The photoelectric device of claim 1, the first electrode further includes a layer of platinum.

* * * * *

SEQUENCE LISTING

```
<160> NUMBER OF SEQ ID NOS: 1

<210> SEQ ID NO 1
<211> LENGTH: 717
<212> TYPE: PRT
<213> ORGANISM: silkworm

<400> SEQUENCE: 1

Asp Ala Ser Gly Ala Val Ile Glu Glu Gln Ile Thr Thr Lys Lys Asn
1               5                   10                  15

His Gly Ile Leu Gly Lys Asn Glu Lys Thr Phe Val Ile Thr Thr Asp
            20                  25                  30

Ser Asp Gly Asn Glu Ser Ile Val Glu Glu Asp Val Leu Met Lys Met
        35                  40                  45

Val Ser Glu Leu Ile Lys Glu Asn Met His Met Lys Leu Tyr Met Glu
    50                  55                  60

Gly Thr Val Asn Asn His His Phe Lys Cys Thr Ser Glu Gly Glu Gly
65                  70                  75                  80

Lys Pro Tyr Glu Gly Thr Gln Thr Met Arg Ala Val Glu Gly Gly Pro
                85                  90                  95

Leu Pro Phe Ala Phe Asp Ile Leu Ala Thr Ser Phe Met Tyr Gly Ser
            100                 105                 110

Lys Val Thr Thr Tyr Glu Asp Gly Gly Val Leu Thr Ala Thr Gln Asp
        115                 120                 125

Thr Ser Leu Gln Asp Gly Cys Leu Ile Tyr Asn Val Lys Ile Arg Gly
    130                 135                 140

Val Asn Phe Pro Ser Asn Gly Pro Val Met Gln Lys Lys Thr Leu Gly
145                 150                 155                 160

Trp Glu Ala Ser Thr Glu Thr Leu Tyr Pro Ala Asp Gly Gly Leu Glu
                165                 170                 175

Gly Arg Met Pro Gly Val Tyr Tyr Val Asp Arg Arg Glu Ala Asp Lys
            180                 185                 190

Glu Thr Tyr Val Glu Gln His Glu Val Ala Val Ala Arg Tyr Cys Asp
        195                 200                 205

Leu Pro Ser Lys Leu Gly His Arg Pro Gln Gln Val Asp Ser Val Ser
    210                 215                 220

Tyr Gly Ala Gly Arg Gly Tyr Gly Gln Gly Ala Gly Ser Ala Ala Ser
225                 230                 235                 240

Ser Val Ser Ser Ala Ser Ser Arg Ser Tyr Asp Tyr Ser Arg Arg Lys
                245                 250                 255

Asn Cys Gly Ile Pro Arg Met Arg Val Lys Thr Phe Val Ile Leu Cys
            260                 265                 270

Cys Ala Leu Gln Tyr Val Ala Tyr Thr Asn Ala Asn Ile Asn Asp Phe
        275                 280                 285
```

```
Asp Glu Asp Tyr Phe Gly Ser Asp Val Thr Val Gln Ser Ser Asn Thr
    290                 295                 300

Thr Asp Glu Ile Ile Arg Asp Ala Ser Gly Ala Val Ile Glu Glu Gln
305                 310                 315                 320

Ile Thr Thr Lys Lys Met Gln Arg Lys Asn Lys Asn His Gly Ile Leu
                325                 330                 335

Gly Lys Asn Glu Lys Met Ile Lys Thr Phe Val Ile Thr Thr Asp Ser
            340                 345                 350

Asp Gly Asn Glu Ser Ile Val Glu Glu Asp Val Leu Met Lys Thr Leu
            355                 360                 365

Ser Asp Gly Thr Val Ala Gln Ser Tyr Val Ala Asp Ala Gly Ala
370                 375                 380

Tyr Ser Gln Ser Gly Pro Tyr Val Ser Asn Ser Gly Tyr Ser Thr His
385                 390                 395                 400

Gln Gly Tyr Thr Ser Asp Phe Ser Thr Ser Ala Ala Val Gly Ala Gly
                405                 410                 415

Ser Ser Gly Arg Met Val Ser Glu Leu Ile Lys Glu Asn Met His Met
            420                 425                 430

Lys Leu Tyr Met Glu Gly Thr Val Asn Asn His His Phe Lys Cys Thr
            435                 440                 445

Ser Glu Gly Glu Gly Lys Pro Tyr Glu Gly Thr Gln Thr Met Arg Ile
450                 455                 460

Lys Ala Val Glu Gly Gly Pro Leu Pro Phe Ala Phe Asp Ile Leu Ala
465                 470                 475                 480

Thr Ser Phe Met Tyr Gly Ser Lys Thr Phe Ile Asn His Thr Gln Gly
                485                 490                 495

Ile Pro Asp Phe Phe Lys Gln Ser Phe Pro Glu Gly Phe Thr Trp Glu
            500                 505                 510

Arg Val Thr Thr Tyr Glu Asp Gly Gly Val Leu Thr Ala Thr Gln Asp
            515                 520                 525

Thr Ser Leu Gln Asp Gly Cys Leu Ile Tyr Asn Val Lys Ile Arg Gly
530                 535                 540

Val Asn Phe Pro Ser Asn Gly Pro Val Met Gln Lys Lys Thr Leu Gly
545                 550                 555                 560

Trp Glu Ala Ser Thr Glu Thr Leu Tyr Pro Ala Asp Gly Gly Leu Glu
                565                 570                 575

Gly Arg Ala Asp Met Ala Leu Lys Leu Val Gly Gly His Leu Ile
            580                 585                 590

Cys Asn Leu Lys Thr Thr Tyr Arg Ser Lys Pro Ala Lys Asn Leu
            595                 600                 605

Lys Met Pro Gly Val Tyr Val Asp Arg Arg Leu Glu Arg Ile Lys
610                 615                 620

Glu Ala Asp Lys Glu Thr Tyr Val Glu Gln His Glu Val Ala Val Ala
625                 630                 635                 640

Arg Tyr Cys Asp Leu Pro Ser Lys Leu Gly His Arg Pro Gln Gln Val
                645                 650                 655

Asp Ser Val Ser Tyr Gly Ala Gly Arg Gly Tyr Gly Gln Gly Ala Gly
            660                 665                 670

Ser Ala Ala Ser Ser Val Ser Ser Ala Ser Arg Ser Tyr Asp Tyr
            675                 680                 685

Ser Arg Arg Asn Val Arg Lys Asn Cys Gly Ile Pro Arg Arg Gln Leu
690                 695                 700
```

-continued

```
Val Val Lys Phe Arg Ala Leu Pro Cys Val Asn Cys Asn
705                 710                 715
```